(12) United States Patent
Baughman et al.

(10) Patent No.: US 8,977,959 B2
(45) Date of Patent: Mar. 10, 2015

(54) VISUALIZATION OF MEDICAL CONDITIONS IN A VIRTUAL UNIVERSE

(75) Inventors: Aaron K. Baughman, Silver Spring, MD (US); Christopher J. Dawson, Arlington, VA (US); Barry M. Graham, Silver Spring, MD (US); David J. Kamalsky, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 876 days.

(21) Appl. No.: 12/410,538

(22) Filed: Mar. 25, 2009

(65) Prior Publication Data

US 2010/0251117 A1 Sep. 30, 2010

(51) Int. Cl.
*G06F 3/00* (2006.01)
*G06N 3/00* (2006.01)
*G06F 19/00* (2011.01)

(52) U.S. Cl.
CPC ............ *G06N 3/006* (2013.01); *G06F 19/3481* (2013.01); *G06F 19/3437* (2013.01)
USPC .......................................... 715/706; 715/757

(58) Field of Classification Search
CPC .... G06F 3/0481; G06F 19/3437; A63F 13/12
USPC ................................................ 715/706, 757
See application file for complete search history.

(56) References Cited

U.S. PATENT DOCUMENTS

| | | | |
|---|---|---|---|
| 6,561,811 B2 * | 5/2003 | Rapoza et al. | 434/236 |
| 6,857,878 B1 * | 2/2005 | Chosack et al. | 434/267 |
| 7,047,296 B1 * | 5/2006 | Safstrom et al. | 709/224 |
| 2002/0107641 A1 * | 8/2002 | Schaeffer et al. | 702/19 |
| 2006/0025931 A1 * | 2/2006 | Rosen et al. | 702/19 |
| 2006/0089543 A1 | 4/2006 | Kim et al. | |
| 2006/0135859 A1 | 6/2006 | Iliff | |
| 2006/0178965 A1 * | 8/2006 | Jung et al. | 705/35 |
| 2007/0050715 A1 | 3/2007 | Behar | |
| 2007/0081718 A1 * | 4/2007 | Rubbert et al. | 382/154 |
| 2008/0014566 A1 * | 1/2008 | Chapman et al. | 434/262 |
| 2008/0020361 A1 * | 1/2008 | Kron et al. | 434/262 |
| 2008/0086501 A1 * | 4/2008 | Levine | 707/103 Y |
| 2008/0214928 A1 * | 9/2008 | Rosales et al. | 600/411 |
| 2010/0127859 A1 * | 5/2010 | Hohmann et al. | 340/540 |

OTHER PUBLICATIONS

Proctor, M. et al., "Object-Oriented Modeling of Patients in a Medical Federation," IEEE Transactions on Information Technology in Biomedicine, vol. 5, No. 3, Sep. 2001.
Lin, F. et al., "Learning Clinical Pathway Patterns by Hidden Markov Model," IEEE Proceedings of the 38th Annual Hawaii International Conference on System Sciences, 2005, pp. 1-7.

* cited by examiner

*Primary Examiner* — Ryan Pitaro
(74) *Attorney, Agent, or Firm* — William E. Schiesser; Hunter E. Webb; Keohane & D'Alessandro PLLC

(57) ABSTRACT

This disclosure provides a system and method to enable the diagnosis, prognosis and emulation of medical conditions using virtual world environments. The system and method combines probabilistic and pattern recognition mechanisms for both real and virtual world applications to increase health care reach and presence within computational environments. The disclosure describes a system and method that uses physiological measurements and behaviors to diagnose a medical condition. Experimental data, either gathered or generated, provide points for emulation. An emulation algorithm increases the feeling of user presence within a virtual world. Avatar behaviors are mapped to scripts which describe the output of the medical diagnosis and prognosis algorithm. Based on proposed treatment plans, emulations can be run, and the appearance of the avatar altered based on the outcome (e.g., improvement, worsening, etc.).

23 Claims, 6 Drawing Sheets

VISUALIZATION OF MEDICAL CONDITIONS IN A VIRTUAL UNIVERSE

FIELD OF THE INVENTION

The present invention generally relates to virtual medical diagnosis. More specifically, the present invention relates to avatar-based virtual medical diagnosis, prognosis, and emulation.

BACKGROUND OF THE INVENTION

As the world population and the cost of health care increases, the number of individuals covered under health insurance is decreasing. Further, access to health care is dependent on wealth, age, place of residence and education. The world wide critical shortage of medical doctors and nurses decrease the probability of a patient receiving appropriate diagnosis and prognosis. In addition, remote patient treatment relies upon accurate knowledge transfer.

SUMMARY OF THE INVENTION

This disclosure provides a system and method to enable the diagnosis, prognosis and emulation of medical conditions using virtual world environments. The system and method combines probabilistic and pattern recognition mechanisms for both real and virtual world applications to increase health care reach and presence within computational environments. The disclosure describes a system and method that uses physiological measurements and behaviors to diagnose a medical condition. Experimental data, either gathered or generated, provide points for emulation. An emulation algorithm increases the feeling of user presence within a virtual world. Avatar behaviors are mapped to scripts which describe the output of the medical diagnosis and prognosis algorithm. Based on proposed treatment plans, emulations can be run, and the appearance of the avatar altered based on the outcome (e.g., improvement, worsening, etc.).

A first aspect of the present invention provides a computer-implemented method for virtual diagnosis comprising: receiving data for a patient in a memory medium; generating an avatar corresponding to the patient using the data, the avatar being generated to have an appearance that reflects a medical condition of the patient based on the data; receiving a treatment plan to address the medical condition in the memory medium; simulating an outcome for the treatment plan; and adjusting the appearance of the avatar to reflect the outcome.

A second aspect of the present invention provides a system for virtual diagnosis comprising: a module for receiving data for a patient in a memory medium; a module for generating an avatar corresponding to the patient using the data, the avatar being generated to have an appearance that reflects a medical condition of the patient based on the data; a module for receiving a treatment plan to address the medical condition in the memory medium; a module for simulating an outcome for the treatment plan; and a module for adjusting the appearance of the avatar to reflect the outcome.

A third aspect of the present invention provides a computer readable medium containing a program product for virtual diagnosis, the computer readable medium comprising instructions for causing a computer system to: receive data for a patient; generate an avatar corresponding to the patient using the data, the avatar being generated to have an appearance that reflects a medical condition of the patient based on the data; receive a treatment plan to address the medical condition; simulate an outcome for the treatment plan; and adjust the appearance of the avatar to reflect the outcome.

A fourth aspect of the present invention provides a method for deploying an application for virtual diagnosis, comprising: deploying a computer infrastructure being operable: receive data for a patient in a memory medium; generate an avatar corresponding to the patient using the data, the avatar being generated to have an appearance that reflects a medical condition of the patient based on the data; receive a treatment plan to address the medical condition in the memory medium; simulate an outcome for the treatment plan; and adjust the appearance of the avatar to reflect the outcome.

A fifth aspect of the present invention provides a data processing system for virtual diagnosis, comprising: a memory medium containing instructions; a bus coupled to the memory medium; and a processor coupled to the bus that when executing the instructions cases the data processing system to: receive data for a patient; generate an avatar corresponding to the patient using the data, the avatar being generated to have an appearance that reflects a medical condition of the patient based on the data; receive a treatment plan to address the medical condition; simulate an outcome for the treatment plan; and adjust the appearance of the avatar to reflect the outcome.

BRIEF DESCRIPTION OF THE DRAWINGS

These and other features of this invention will be more readily understood from the following detailed description of the various aspects of the invention taken in conjunction with the accompanying drawings in which.

Figure 1:
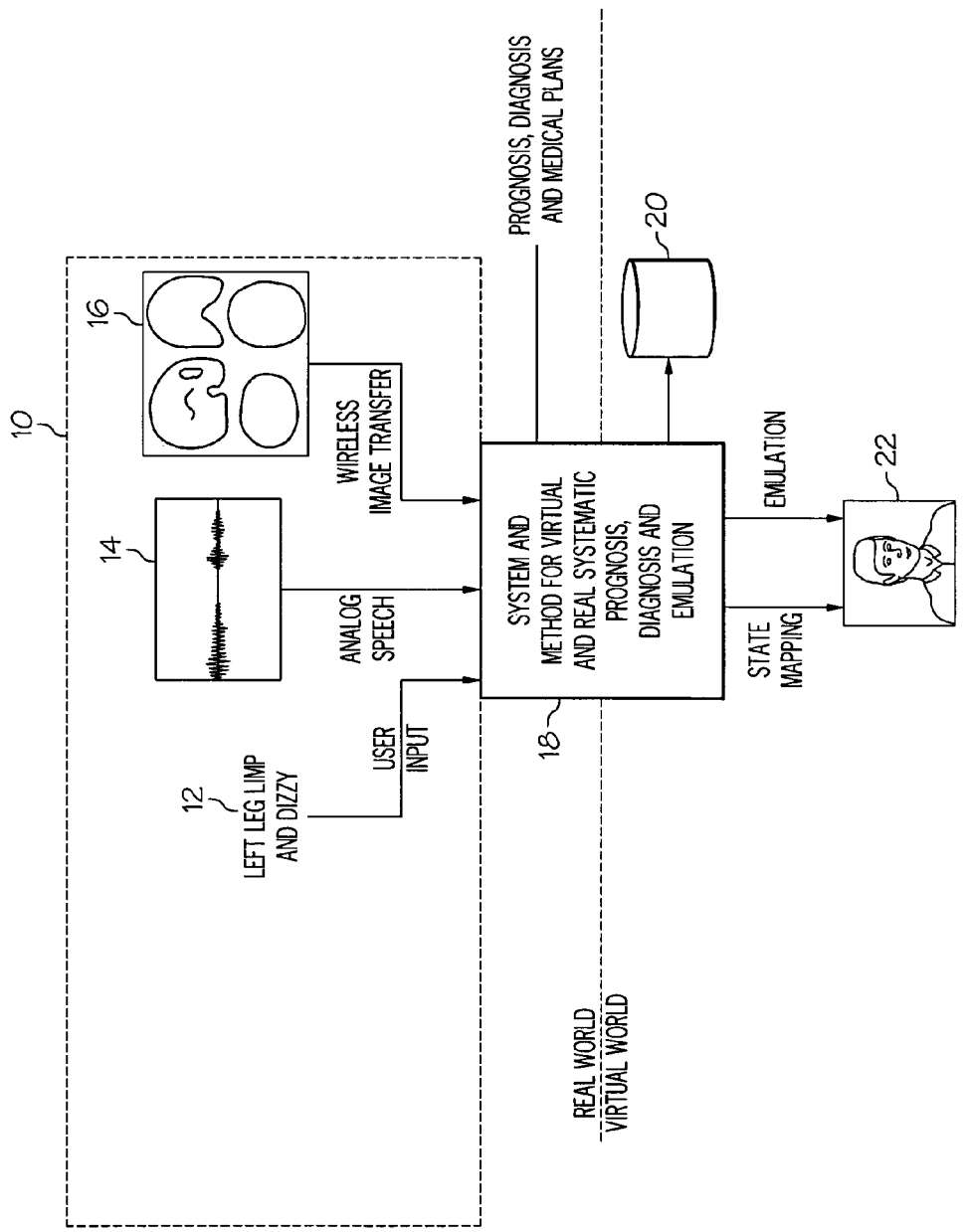
FIG. 1 depicts a high level block diagram according to the present invention.

The drawings are not necessarily to scale. The drawings are merely schematic representations, not intended to portray specific parameters of the invention. The drawings are intended to depict only typical embodiments of the invention, and therefore should not be considered as limiting the scope of the invention. In the drawings, like numbering represents like elements.

DETAILED DESCRIPTION OF THE INVENTION

For convenience, the detailed description of the invention has the following sections:

I. Overview
II. Key Concepts
III. Illustrative Implementation
IV. Computerized Implementation I. Overview As indicated above, this disclosure provides a system and method to enable the diagnosis, prognosis and emulation of medical conditions using virtual world environments. The system and method combines probabilistic and pattern recognition mechanisms for both real and virtual world applications to increase health care reach and presence within computational environments. The disclosure describes a system and method that uses physiological measurements and behaviors to diagnose a medical condition. Experimental data, either gathered or generated, provide points for emulation. An emulation algorithm increases the feeling of user presence within a virtual world. Avatar behaviors are mapped to scripts which describe the output of the medical diagnosis and prognosis algorithm.

For example, if a user has a limp while walking, the system and method can provide a diagnosis, prognosis and emulation of the condition. The user (either the patient or the doctor) enters knowledge describing the injury and uploads x-ray images of the bone for pattern recognition. A "belief network," modeled from knowledge bases with pattern recognition algorithms, provides the user with a diagnosis and a series of medical plans with a corresponding prognosis. The diagnosis is mapped to the user's avatar where an emulation provides feedback as to the results of prescribed actions.

This invention provides a mechanism to simulate ailments within a multi-user virtual world. The emulations allow patients to display their physical conditions through an avatar within the context of a virtual world. In addition, medical practitioners will be able to enter the virtual world through the use of avatars to view emulated physical conditions and demonstrate the outcome of a completed prescribed plan. The increase in user presence within a virtual world through an avatar enables the notion of virtual clinics. Therefore this invention solves the problem that requires a medical doctor to be physically located next to a patient to perform diagnosis. Further, the invention solves the problem of conveying future symptoms and outcomes through the use of a representative avatar.

II. Key Concepts

A. Implementation of a Probabilistic Conditional Equation—This disclosure describes an algorithm that combines physiological measurements and behavioral traits with a diagnosis, diagnosis and emulation virtual scripts. The invention can use multiple algorithms including a Hidden Markov Model (HMM) to determine the probability of ailments given measurements. For example, each HMM node determines the probability of a physiological measurement given an ailment. The given measurements can be and not limited to family history, skin conditions, recent injuries, other visible signs, stomach sickness, gait patterns and actual measurements from medical instrumentation.

B. Virtual Emulation and Simulation—The combination of determined ailments and potential prognoses and diagnoses are emulated within a staging virtual clinic. Skins or graphical overlays and behavior scripts are mapped to ailments and outputs of the probabilistic conditional equation. A threshold bar determines which outputs are most plausible. Multiple avatars are spawned, one for each potential current state. A user picks or modifies an existing avatar that closely matches their real world state. All of the behavior scripts and skins are moved from the selected spawned avatar to a user's avatar. In addition, the chosen spawned avatar progresses through stages of a sickness. When a branch point within the simulation is created, the user can collaborate with other users in the world on choosing medications and prescribed plans that fit their needs. Accordingly, the results of such actions are simulated and shared with all participants within the virtual world. After a prescribed plan is chosen, a user can move their avatar that represents their current physical state to a virtual clinic.

Along these lines, assume a patient has jaundice or yellow staining of the skin. Further assume that the algorithm and system of the present invention determines the user has a high risk of high bile pigment associated with hepatitis. As a result, yellow skins are placed on the user's avatar. Fatigue momentum scalars that change the avatar's rate of movement with additional aesthetic scripts are tagged with the medical plan of no action. The aforementioned behavioral, physiological and cognitive processes are mapped to other medical plans produced from the invention described in the disclosure. A user selects which medical plan the avatar should follow while watching the affects within the virtual world. A time step scale selected by the user determines the rate of evolution. If desired, multiple avatars, each following disparate medical plans, are spawned within the virtual world for parallel evolution. This allows a patient to receive customized, professionally informed and correct medical treatment without leaving home, thereby increasing convenience for the patient, giving better diagnoses, and preventing the spread of contagious illness.

III. Illustrative Implementation

Referring to FIG. 1, a high level block diagram is shown. As depicted, data 10 for a patient in the form of symptoms 12, speech 14, image data 16 (e.g., MRI, CT, X-RAY, etc., collectively referred to as patient data 10) is received by a virtual diagnosis and emulation system 18 (hereinafter VDE system 18). Using a Probabilistic Conditional Equation (i.e., a knowledge base is represented within a graph structure of a Hidden Markov Model (HMM)). Using patient data VDE system 18 will consult one or more knowledge bases 20 to determine a diagnosis, prognosis, and set (e.g., at least one) of treatment plans. In addition, VDE system 18 will map the patient data 10, diagnosis and/or prognosis to physical features and output a corresponding avatar 22 (thus transforming patient data 10 into an avatar). As such, avatar 22 will have a graphical appearance reflective of medical conditions of the patient. The appearance of avatar 22 will be altered based on changes in the patient's condition, and/or the outcome of any treatment plans. Along these lines, VDE system 18 can provide emulations so that multiple treatment plans could be followed (e.g., before treatment is actually administered to the patient). Based on the simulated outcome(s) of the virtual treatment plan(s), the appearance of avatar 22 can be adjusted. In one embodiment, a different avatar 22 could be rendered for each proposed treatment plan. This allows a comparison of the avatars as their appearances change in light of their respective treatment plans.

Under the present invention a knowledge base, such as knowledge base 20, can be represented within a graph structure of a Hidden Markov Model (HMM). All possible HMM states are evaluated with associated inputs for each HMM state. Each HMM state is a probabilistic neural network that classifies input images, signals or user input. Each neural network is trained on exact state input and related states. As a result, the input into the neural network is classified. A staging server might utilize a feed forward back propagation algorithm to learn given templates or patterns. As an example, the patterns learned could correspond to a subject's gait. A bank of networks are available for each HMM state. The networks are separated with respect to the type of input required. Network A requires images while network B requires user input.

Figure 2:
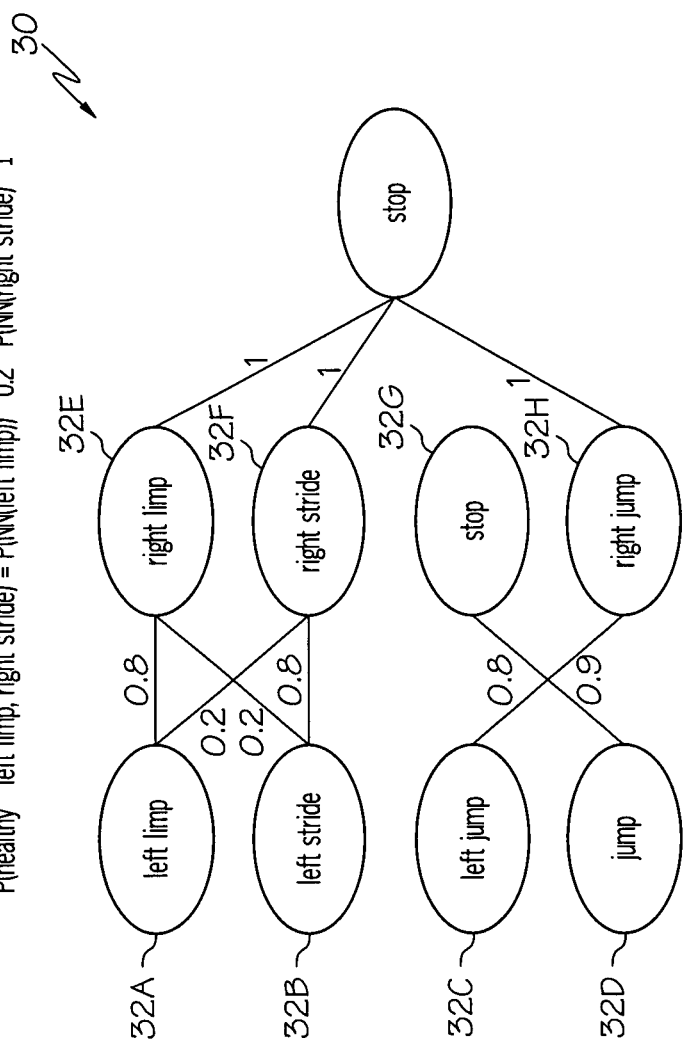
FIG. 2 depicts an electronic device having power reserve capabilities according to the present invention.

Under the present invention, each node within a Markov Model represents a probabilistic neural network (PNN). FIG. 2 shows an example of a probabilistic neural network 30 of nodes 32A-H. The equations for a 2 layer PNN is as follows:

Input Vector:

$$X^p = (X^p_1, \ldots, X^p_n)$$

Target Vector:

$$T^p = (T^p_1, \ldots, T^p_n)$$

The equations are for a feed forward back propagation 1 input, 1 hidden and 1 output layer.
Feed Forward Equations:
Output of the ith input node when the pith input vector is presented.

$$O^{p,o}_i = x^p_i)$$

Input of the jth hidden node at level 1.

$$I^{p,1}_j = \sum_{i=1}^{n_j+1} w^1_{j,i} O^{p,O}_i$$

Input to the jth hidden node at level 1.

$$O^{p,1}_j = f\left(\sum_{i=1}^{n_j+1} w^1_{j,i} O^{p,O}_i\right)$$

The mean squared error function.

$$E = 0.5 \sum_{p=1}^{n_p} \sum_{i=1}^{n_o} (Tp1 \cdot O^{p,m}_i)^2$$

Input to the jth hidden node at level 1.

$$\partial(E/\partial w^2_{i,j}) = -\sum_{p=1}^{n_p} (\zeta^i_{p,2} O^{p,1}_i)$$

$$\zeta^{p,2}_i = (T^p_i - O^{p,2}_i) O^{p,2}_i (1 - O^{p,2}_i)$$

Learning equation for the second tier weights:

$$w^2_{ij}(t+1) = w^2_{ij}(t) + N \sum_{p=1}^{n_p} \zeta^{p,2}_i O^j_{p1} + a\Delta w^2_{ij}(t)$$

Figure 3:
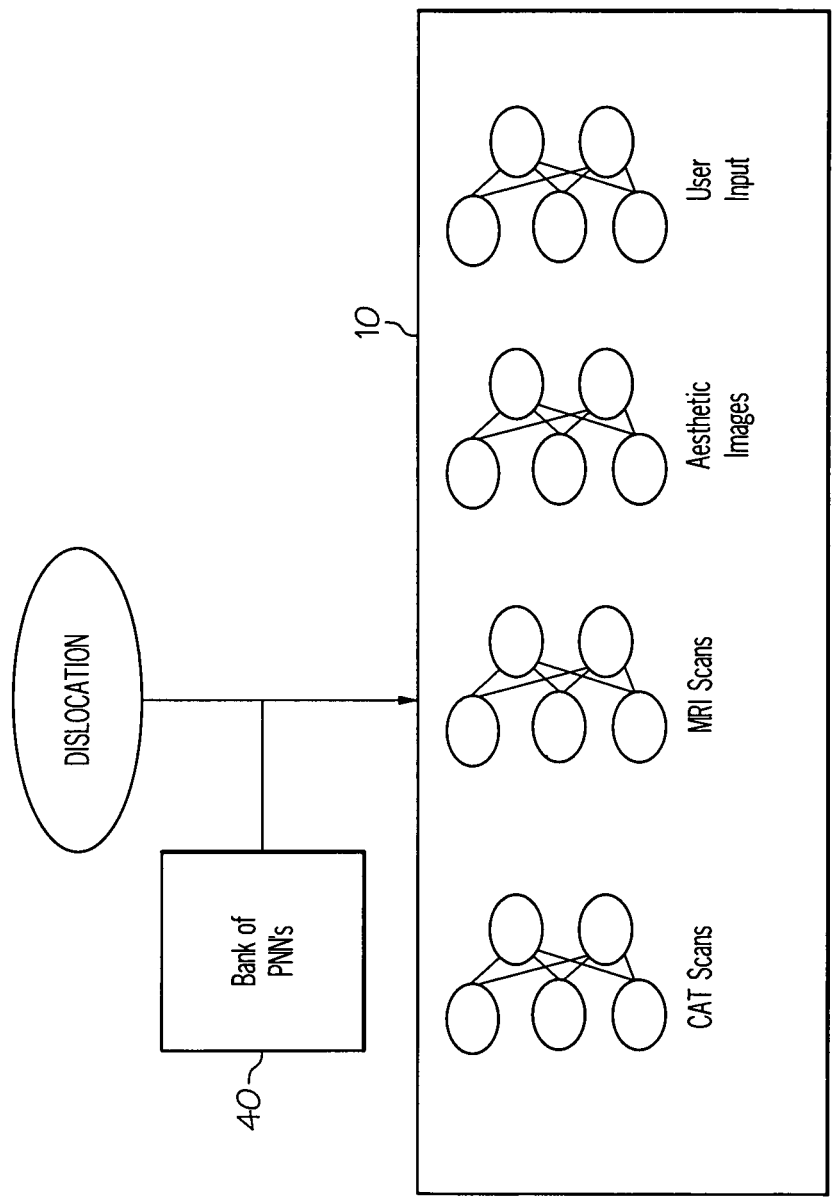
FIG. 3 depicts a bank of probabilistic neural networks according to the present invention.

FIG. 3 shows a bank PNNs 40. As shown, a diagnosis of dislocation is made when considering patient data 10 in view of bank of PNNs 40. Under the present invention, each state within the Hidden Markov Model is decomposed by a bank of probabilistic neural networks. The neural networks have been trained on a set of data. For example, each network is trained on either CAT scans, MRI scans, Aesthetic images or user input. As a result, the images are classified with respect to training data.

Figure 4:
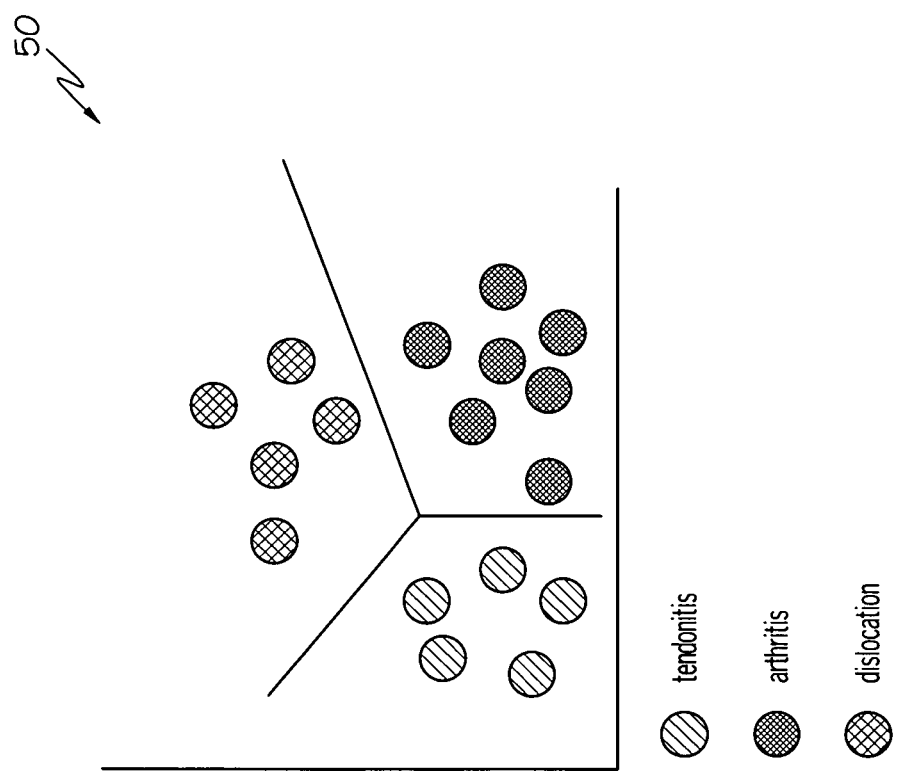
FIG. 4 depicts a graph of possible medical diagnoses according to the present invention.

The data is separable into classes following traditional pattern recognition. The neural network trained on a given dataset with a prior determination on a target goal, produces classification capability. Results in a graph 50 are shown in FIG. 4. As depicted, three possible diagnoses for the patient in this example, are tendonitis, arthritis, and/or dislocation.

As discussed above, the present invention provides emulation so that one or more treatment plans can be virtually simulated on the avatar before treatment is actually administered to the patient. Using the example of FIG. 4 above, one or more treatment plans can be designed for any of the three diagnoses. Each treatment plans can be administered to a different rendering/instance of the avatar. The appearance of the instance(s) can be altered based on the predicted reactions thereof. Such reactions would be predicted from one or more knowledge bases of previously medical data, diagnoses, and/or results.

Under the present invention, the system and method for virtual and real systemic prognosis, diagnosis and emulation can be the middleware between the real and virtual world. As diagnosis and prognosis recognition is performed, a real world state is mirrored onto an avatar. The twining of state not only increases a user's presence within a virtual world but also provides an environment for emulation. As the avatar progresses through virtual experiences, the state of the avatar changes based upon a prognosis plan. Behavior scripts, skins and prims are mapped to an avatar from a real world user or avatar emulation.

Figure 5:
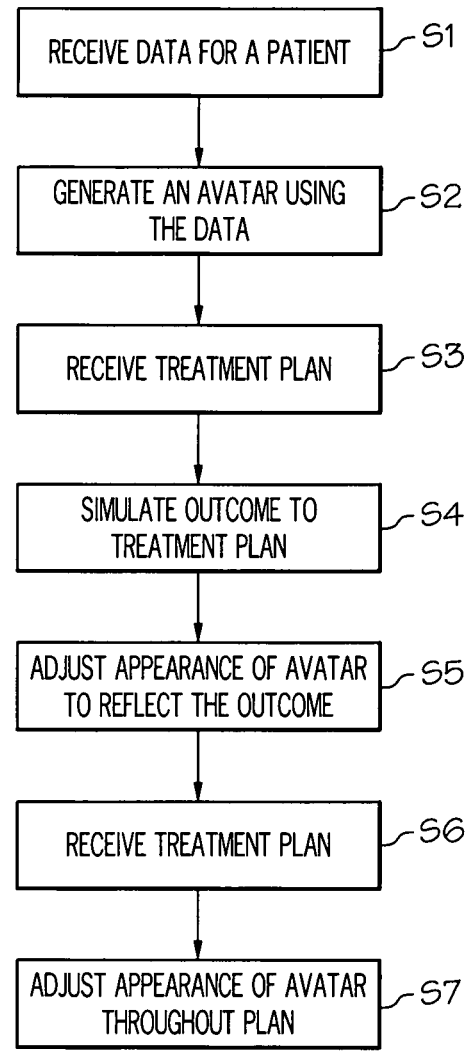
FIG. 5 depicts a method flow diagram according to the present invention.

Referring to FIG. 5, a method flow diagram according to the present invention is shown. As depicted, in step S1, data for a patient is received. In step S2, an avatar corresponding to the patient using the data is generated. The avatar is generated to have an appearance that reflects a medical condition of the patient based on the data (thus transforming the medical data into an image). In step S3 a treatment plan to address the medical condition is received. In step S4, an outcome for the treatment plan is simulated. In step S5, the appearance of the avatar is adjusted to reflect the outcome. In step S6, a selection of a treatment plan is received, and in step S7, the appearance of the avatar is adjusted as the patient progresses through the treatment plan.

IV. Computerized Implementation

Figure 6:
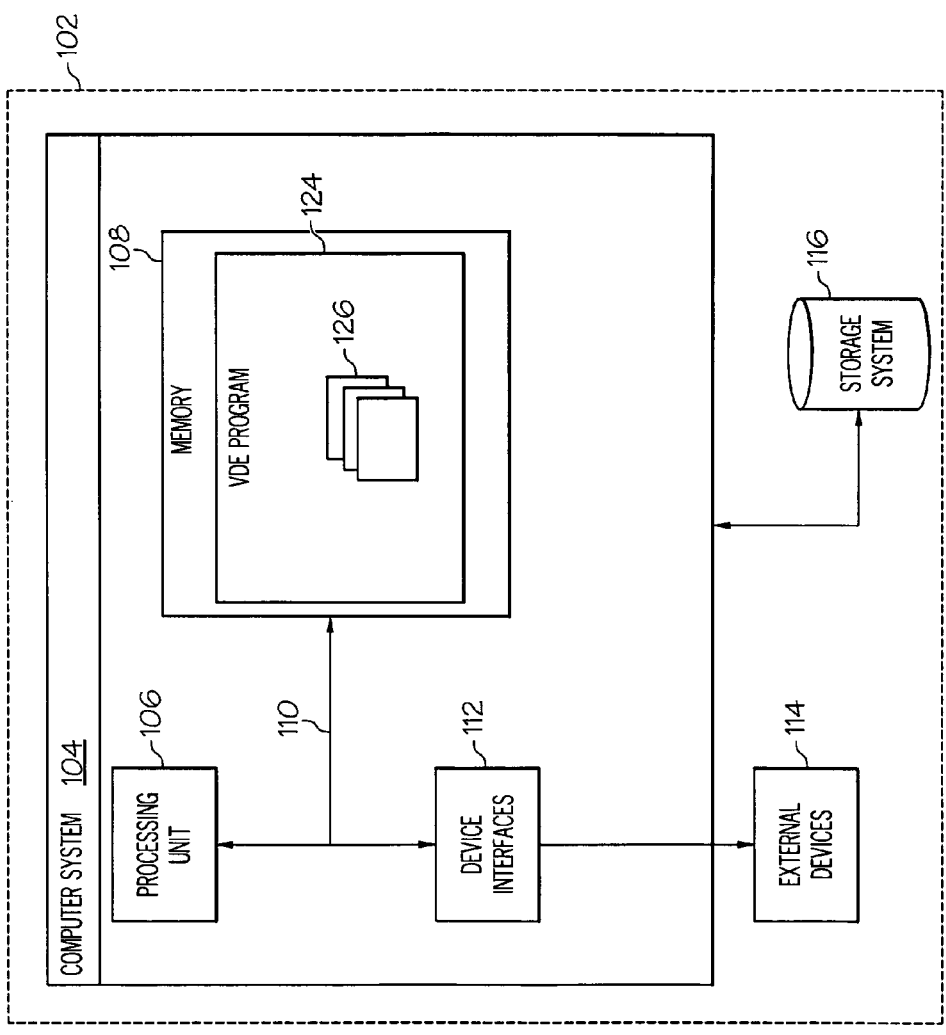
FIG. 6 depicts a more specific computerized implementation according to the present invention.

Referring now to FIG. 6, a computerized implementation 100 of the present invention is shown. As depicted; implementation 100 includes computer system 104 deployed within a computer infrastructure 102. This is intended to demonstrate, among other things, that the present invention could be implemented within a network environment (e.g., the Internet, a wide area network (WAN), a local area network (LAN), a virtual private network (VPN), etc.), or on a standalone computer system. In the case of the former, communication throughout the network can occur via any combination of various types of communications links. For example, the communication links can comprise addressable connections that may utilize any combination of wired and/or wireless transmission methods. Where communications occur via the Internet, connectivity could be provided by conventional TCP/IP sockets-based protocol, and an Internet service provider could be used to establish connectivity to the Internet. Still yet, computer infrastructure 102 is intended to demonstrate that some or all of the components of implementation 100 could be deployed, managed, serviced, etc. by a service provider who offers to implement, deploy, and/or perform the functions of the present invention for others.

Computer system 104 is intended to represent any type of computer system that may be implemented in deploying/realizing the teachings recited herein. It should be understood that any other computers implemented under the present invention will have similar components, but may perform different functions/have different software. As shown, computer system 104 includes a processing unit 106, a memory 108, a bus 110, and device interfaces 112. Further, computer system 104 is shown communicating with one or more external devices 114 that communicate with bus via device interfaces. In general, processing unit 106 executes computer program code, such VDE system/program 124 (block 18 in FIG. 1), which is stored in memory 108 and/or storage system 116. While executing computer program code, processing unit 106 can read and/or write data to/from memory 108, storage system 116, and/or device interfaces 112. Bus 110 provides a communication link between each of the components in computer system 104. Although not shown, computer system 104 could also include I/O interfaces that communicate with: one or more external devices such as a kiosk, a checkout station, a keyboard, a pointing device, a display, etc.); one or more devices that enable a user to interact with computer system 104; and/or any devices (e.g., network card, modem, etc.) that enable computer system 104 to communicate with one or more other computing devices. Although not shown, computer system 104 could contain multiple processing units.

Computer infrastructure 102 is only illustrative of various types of computer infrastructures for implementing the invention. For example, in one embodiment, computer infrastructure 102 comprises two or more computing devices (e.g., a server cluster) that communicate over a network to perform the various processes of the invention. Moreover, computer system 104 is only representative of various possible computer systems that can include numerous combinations of hardware. To this extent, in other embodiments, computer system 104 can comprise any specific purpose computing article of manufacture comprising hardware and/or computer program code for performing specific functions, any computing article of manufacture that comprises a combination of specific purpose and general purpose hardware/software, or the like. In each case, the program code and hardware can be created using standard programming and engineering techniques, respectively. Moreover, processing unit 106 may comprise a single processing unit, or be distributed across one or more processing units in one or more locations, e.g., on a client and server. Similarly, memory 108 and/or storage system 116 can comprise any combination of various types of data storage and/or transmission media that reside at one or more physical locations. Further, device interfaces 112 can comprise any module for exchanging information with one or more external devices. Still further, it is understood that one or more additional components (e.g., system software, math co-processing unit, etc.) not shown in FIG. 6 can be included in computer system 104.

Storage system 116 can be any type of system (e.g., storage units 70A-N of FIG. 6) capable of providing storage for information under the present invention. To this extent, storage system 116 could include one or more storage devices such as magnetic disk drive or an optical disk drive. In another embodiment, storage system 116 includes data distributed across, for example, a local area network (LAN), wide area network (WAN) or a storage area network (SAN) (not shown). In addition, although not shown, additional components, such as cache memory, communication systems, system software, etc., may be incorporated into computer system 104. Shown in memory 108 of computer system 104 is VDE system/program 124, which has a set of modules 126. Set of modules 126 generally provide the functions of the present invention as described herein.

While shown and described herein as virtual medical diagnosis and emulation, it is understood that the invention further provides various alternative embodiments. For example, in one embodiment, the invention provides a computer-readable/useable medium that includes computer program code to enable a computer infrastructure to variable energy pricing. To this extent, the computer-readable/useable medium contains program code that implements each of the various processes of the invention. It is understood that the terms computer-readable medium or computer useable medium comprises one or more of any type of physical embodiment of the program code. In particular, the computer-readable/useable medium can comprise program code embodied on one or more portable storage articles of manufacture (e.g., a compact disc, a magnetic disk, a tape, etc.), on one or more data storage portions of a computing device, such as memory 108 (FIG. 6) and/or storage system 116 (FIG. 6) (e.g., a fixed disk, a read-only memory, a random access memory, a cache memory, etc.), and/or as a data signal (e.g., a propagated signal) traveling over a network (e.g., during a wired/wireless electronic distribution of the program code).

In another embodiment, the invention provides a business method that performs the process of the invention on a subscription, advertising, and/or fee basis. That is, a service provider, such as a Solution Integrator, could offer to provide virtual medical diagnosis and emulation. In this case, the service provider can create, maintain, support, etc., a computer infrastructure, such as computer infrastructure 102 (FIG. 6) that performs the process of the invention for one or more customers. In return, the service provider can receive payment from the customers under a subscription and/or fee agreement and/or the service provider can receive payment from the sale of advertising content to one or more third parties.

In still another embodiment, the invention provides a computer-implemented method for virtual medical diagnosis and emulation. In this case, a computer infrastructure, such as computer infrastructure 102 (FIG. 6), can be provided and one or more systems for performing the process of the invention can be obtained (e.g., created, purchased, used, modified, etc.) and deployed to the computer infrastructure. To this extent, the deployment of a system can comprise one or more of: (1) installing program code on a computing device, such as computer system 104 (FIG. 6), from a computer-readable medium; (2) adding one or more computing devices to the computer infrastructure; and (3) incorporating and/or modifying one or more existing systems of the computer infrastructure to enable the computer infrastructure to perform the process of the invention.

As used herein, it is understood that the terms "program code" and "computer program code" are synonymous and mean any expression, in any language, code or notation, of a set of instructions intended to cause a computing device having an information processing capability to perform a particular function either directly or after either or both of the following: (a) conversion to another language, code or notation; and/or (b) reproduction in a different material form. To this extent, program code can be embodied as one or more of: an application/software program, component software/a library of functions, an operating system, a basic device system/driver for a particular computing and/or device, and the like.

A data processing system suitable for storing and/or executing program code can be provided hereunder and can include at least one processor communicatively coupled, directly or indirectly, to memory elements through a system bus. The memory elements can include, but are not limited to, local memory employed during actual execution of the program code, bulk storage, and cache memories that provide temporary storage of at least some program code in order to reduce the number of times code must be retrieved from bulk storage during execution. Input/output or device devices (including, but not limited to, keyboards, displays, pointing devices, etc.) can be coupled to the system either directly or through intervening device controllers. It is inherent herein that the present invention is tied to at least one machine (e.g., computer system 102), and/or transforms at least one article (e.g., patient data, avatars, etc.) and/or data representative of one article (e.g. imaging data).

Network adapters also may be coupled to the system to enable the data processing system to become coupled to other data processing systems, remote printers, storage devices, and/or the like, through any combination of intervening private or public networks. Illustrative network adapters include, but are not limited to, modems, cable modems and Ethernet cards.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:

1. A computer-implemented method for virtual diagnosis comprising:
    receiving data, which includes patient imaging data, for a patient in a memory medium, the patient being an actual human patient that has a current medical condition;
    generating a set of avatars corresponding to the actual human patient using the data, each avatar of the set of avatars being generated to have an appearance of the patient and to emulate a current physical state and movements of the patient based on the medical condition indicated by the data;
    providing an interface that enables the patient to select an avatar that most closely matches the physical state of the patient from the set of avatars and to modify the avatar to more closely match the physical state of the patient;
    receiving in the memory medium a treatment plan from a remote medical practitioner in a virtual clinic to address the medical condition of the patient in the memory medium;
    simulating an outcome for the patient based upon the treatment plan, said simulating comprising use of probabilistic and pattern recognition mechanisms for analysis of a combination of said treatment plan and potential prognoses and diagnoses to identify the outcome as a most plausible outcome; and
    adjusting the appearance of the avatar to reflect a series of predicted changes in the physical state of the patient over time based on the simulating of the outcome.

2. The method of claim 1, the data comprising physical measurements, medical history, and symptoms.

3. The method of claim 1, the generating comprising using a set of algorithms to determine a probability of ailments given the data.

4. The method of claim 3, the set of algorithms comprising a Hidden Markov Model.

5. The method of claim 3, further comprising mapping graphical overlays and behavior scripts to ailments and outputs of the set of algorithms.

6. The method of claim 5, further comprising using a threshold bar to determine the outputs.

7. The method of claim 1, further comprising:
    receiving a selection of a treatment plan; and
    adjusting the appearance of the avatar as the patient progresses through the treatment plan.

8. A computer-implemented system for virtual diagnosis comprising:
    a module for receiving data, which includes patient imaging data, for a patient in a memory medium, the patient being an actual human patient that has a current medical condition;
    a module for generating a set of avatars corresponding to the actual human patient using the data, each avatar of the set of avatars being generated to have an appearance of the patient and to emulate a current physical state and movements of the patient based on the medical condition indicated by the data;
    a module for providing an interface that enables the patient to select an avatar that most closely matches the physical state of the patient from the set of avatars and to modify the avatar to more closely match the physical state of the patient;
    a module for receiving a treatment plan from a remote medical practitioner in a virtual clinic to address the medical condition of the patient in the memory medium;
    a module for simulating an outcome for the patient based upon the treatment plan, said simulating comprising use of probabilistic and pattern recognition mechanisms for analysis of a combination of said treatment plan and potential prognoses and diagnoses to identify the outcome as a most plausible outcome; and
    a module for adjusting the appearance of the avatar to reflect a series of predicted changes in the physical state of the patient over time based on the simulating of the outcome.

9. The system of claim 8, the data comprising physical measurements, medical history, and symptoms.

10. The system of claim 8, the generating comprising using a set of algorithms to determine a probability of ailments given the data.

11. The system of claim 10, the set of algorithms comprising a Hidden Markov Model.

12. The system of claim 10, further comprising mapping graphical overlays and behavior scripts to ailments and outputs of the set of algorithms.

13. The system of claim 12, further comprising using a threshold bar to determining the outputs.

14. The system of claim 8, further comprising:
    receiving a selection of a treatment plan; and
    adjusting the appearance of the avatar as the patient progresses through the treatment plan.

15. A computer readable storage device containing a program product for virtual diagnosis, the computer readable medium comprising instructions for causing a computer system to:
    receive data, which includes patient imaging data, for a patient, the patient being an actual human patient that has a current medical condition;
    generate a set of avatars corresponding to the actual human patient using the data, each avatar of the set of avatars being generated to have an appearance of the patient and to emulate a current physical state and movements of the patient based on the medical condition indicated by the data;
    provide an interface that enables the patient to select an avatar that most closely matches the physical state of the patient from the set of avatars and to modify the avatar to more closely match the physical state of the patient;
    receive a treatment plan from a remote medical practitioner in a virtual clinic to address the medical condition of the patient;
    simulate an outcome for the patient based upon the treatment plan, said simulating comprising use of probabilistic and pattern recognition mechanisms for analysis of a combination of said treatment plan and potential prognoses and diagnoses to identify the outcome as a most plausible outcome; and
    adjust the appearance of the avatar to reflect a series of predicted changes in the physical state of the patient over time based on the simulating of the outcome.

16. The computer readable storage device containing the program product of claim 15, the data comprising physical measurements, medical history, and symptoms.

17. The computer readable storage device containing the program product of claim 15, the computer readable medium further comprising instructions for causing the computer system to use a set of algorithms to determine a probability of ailments given the data.

18. The computer readable storage device containing the program product of claim 17, the set of algorithms comprising a Hidden Markov Model.

19. The computer readable storage device containing the program product of claim 17, the computer readable medium comprising instructions for causing the computer system to map graphical overlays and behavior scripts to ailments and outputs of the set of algorithms.

20. The computer readable storage device containing the program product of claim 19, the computer readable medium further comprising instructions for causing the computer system to use a threshold bar to determining the outputs.

21. The computer readable storage device containing the program product of claim 15, the computer readable medium further comprising instructions for causing the computer system to:
  receive a selection of a treatment plan; and
  adjust the appearance of the avatar as the patient progresses through the treatment plan.

22. A method for deploying an application for virtual diagnosis, comprising:
  deploying a computer infrastructure being operable to:
    receive data, which includes patient imaging data, for a patient in a memory medium, the patient being an actual human patient that has a current medical condition;
    generate a set of avatars corresponding to the actual human patient using the data, each avatar of the set of avatars being generated to have an appearance of the patient and to emulate a current physical state and movements of the patient based on the medical condition indicated by the data;
    provide an interface that enables the patient to select an avatar that most closely matches the physical state of the patient from the set of avatars and to modify the avatar to more closely match the physical state of the patient;
    receive a treatment plan from a remote medical practitioner in a virtual clinic to address the medical condition of the patient in the memory medium;
    simulate an outcome for the patient based upon the treatment plan, said simulating comprising use of probabilistic and pattern recognition mechanisms for analysis of a combination of said treatment plan and potential prognoses and diagnoses to identify the outcome as a most plausible outcome; and
    adjust the appearance of the avatar to reflect a series of predicted changes in the physical state of the patient over time based on the simulating of the outcome.

23. A data processing system for virtual diagnosis, comprising:
  a memory medium containing instructions;
  a bus coupled to the memory medium; and
  a processor coupled to the bus that when executing the instructions causes the data processing system to:
    receive data, which includes patient imaging data, for a patient, the patient being an actual human patient that has a current medical condition;
    generate a set of avatars corresponding to the actual human patient using the data, each avatar of the set of avatars being generated to have an appearance of the patient and to emulate a current physical state and movements of the patient based on the medical condition indicated by the data;
    provide an interface that enables the patient to select an avatar that most closely matches the physical state of the patient from the set of avatars and to modify the avatar to more closely match the physical state of the patient;
    receive a treatment plan from a remote medical practitioner in a virtual clinic to address the medical condition of the patient;
    simulate a set of outcomes for the patient based upon the treatment plan, said simulating comprising use of probabilistic and pattern recognition mechanisms for analysis of a combination of said treatment plan and potential prognoses and diagnoses to determine which outcome is most plausible; and
    adjust the appearance of the avatar to reflect a series of predicted changes in the physical state of the patient over time based on the simulating of the outcome.

* * * * *